United States Patent [19]

Banks et al.

[11] Patent Number: 4,567,159

[45] Date of Patent: Jan. 28, 1986

[54] OLEFIN METATHESIS CATALYST

[75] Inventors: Robert L. Banks; Simon G. Kukes, both of Bartlesville, Okla.

[73] Assignee: Phillips Petroleum Company, Bartlesville, Okla.

[21] Appl. No.: 649,341

[22] Filed: Sep. 11, 1984

Related U.S. Application Data

[62] Division of Ser. No. 536,819, Sep. 28, 1983, Pat. No. 4,504,694.

[51] Int. Cl.$^4$ .................. B01J 31/02; B01J 27/14; B01J 27/02; B01J 27/06
[52] U.S. Cl. ........................ 502/219; 502/158; 502/210; 502/211; 502/220; 502/228; 502/214
[58] Field of Search ............... 502/158, 210, 211, 220, 502/219, 228, 214

[56] References Cited

U.S. PATENT DOCUMENTS

| | | | |
|---|---|---|---|
| 3,544,647 | 12/1970 | Pennella | 260/683 |
| 3,692,694 | 9/1972 | Kravitz et al. | 502/228 X |
| 3,692,697 | 9/1972 | Kravitz et al. | 502/220 |
| 3,707,581 | 12/1972 | Heckelsberg | 260/683 D |
| 3,787,329 | 1/1974 | Covitt | 502/158 |
| 4,080,398 | 3/1978 | Basset et al. | 260/683 D |

Primary Examiner—D. E. Gantz
Assistant Examiner—William G. Wright
Attorney, Agent, or Firm—Howard D. Doescher

[57] ABSTRACT

Olefins are converted into other olefins having different numbers of carbon atoms by contact with a catalyst comprising an inorganic refractory material containing at least one of tungsten oxide and molybdenum oxide and a promoting amount of at least one treating agent selected from chlorinated silicon compounds, thionyl chloride, and sulfuryl chloride under conditions suitable for the treating agent to promote the activity of tungsten and molybdenum oxides for the disproportionation reaction.

10 Claims, No Drawings

OLEFIN METATHESIS CATALYST

This application is a division of application Ser. No. 536,819, filed Sept. 28, 1983, now U.S. Pat. No. 4,504,694.

BACKGROUND OF INVENTION

This invention relates to the disproportionation (metathesis) of olefins. In accordance with one aspect, this invention relates to a catalyst suitable for use in the disproportionation of olefinic hydrocarbons. In accordance with another aspect, this invention relates to a process for the disproportionation of olefinic hydrocarbons. In accordance with a further aspect, this invention relates to a catalyst suitable for use in the disproportionation of olefins comprising at least one of molybdenum oxide and tungsten oxide, an inorganic refractory material, and at least one chlorine-containing compound. In accordance with a further aspect, this invention relates to a catalyst suitable for use in the disproportionation of olefins comprising an inorganic refractory material and at least one of molybdenum oxide and tungsten oxide promoted with at least one of a chlorinated silicon compound, thionyl chloride, and sulfuryl chloride. In accordance with another aspect, this invention relates to a process for the disproportionation of olefinic hydrocarbons with a disproportionation catalyst as hereinbefore described under conditions of temperature and pressure which effect disproportionation of the feed.

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons.

Among the catalysts that have been developed for disproportionation are those comprising inorganic refractory materials containing a catalytic amount of at least one of molybdenum oxide and tungsten oxide. The present invention is based upon the discovery of a way to improve the activity of such a catalyst.

Accordingly, an object of this invention is to provide a method for the conversion of olefins.

Another object of this invention is to provide a catalyst for the conversion of olefins.

Still another object of this invention is to provide a method for converting olefins to olefins having different numbers of carbon atoms than the feed hydrocarbons.

Still another object is to provide a method for improving the activity of a disproportionation catalyst for the conversion of olefins into olefins having different numbers of carbon atoms than the feed hydrocarbons.

Other aspects, objects and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising an inorganic refractory material containing a catalytically effective amount of at least one of molybdenum oxide and tungsten oxide is improved by contacting the catalyst with a promoting amount of at least one promoting or treating agent selected from chlorinated silicon compounds, thionyl chloride and sulfuryl chloride under conditions suitable for the treating agent to promote the activity of molybdenum and tungsten oxides.

Further, in accordance with a specific embodiment of the present invention, a disproportionation (metathesis) catalyst comprising an inorganic refractory material, such as silica or thorium phosphate, containing a catalytically effective amount of tungsten oxide is improved by contacting the tungsten oxide catalyst with a promoting and activating amount of at least one chlorinating agent, such as chlorinated silicon compounds, thionyl chloride, or sulfuryl chloride, under conditions suitable for the chlorinating agent to promote the activity of tungsten oxide.

Also according to the invention, a process is provided for the disproportionation of an olefinic hydrocarbon by contacting the same with a disproportionation catalyst as hereinbefore described under conditions of temperature and pressure which effect disproportionation of the feed.

The inorganic refractory material comprises a solid usually containing a major proportion of alumina or silica and the like. Such materials are commonly known as refractory oxides and include, for example, silica, alumina, magnesia-alumina, silica-alumina, titania-alumina, zirconia-alumina, alumina-titania-zirconia, thoria, aluminum phosphate, zirconium phosphate, calcium phosphate, magnesium phosphate, thorium phosphate, and titanium phosphate. Preferred refractory metal oxides are silica refractory oxides, i.e., refractory oxides containing a substantial proportion of silica, e.g., at least 90 percent by weight of silica, preferably at least 99 percent of silica although still larger proportions of silica can be used. Generally, the refractory oxide has a surface area of at least 10 m$^2$/g and preferably the surface area is from about 25 m$^2$/g to 800 m$^2$/g.

Molybdenum oxide and tungsten oxide can be combined with the refractory material in any conventional manner such as dry mixing, impregnation from a diluent, ion-exchange or the like. The oxides can be added directly or in the form of molybdenum or tungsten compounds that can be converted to oxides by calcination.

Preferred combinations of the above refractory materials with the oxides of molybdenum and tungsten materials include (1) silica or thoria promoted by the oxide, or a compound convertible to an oxide by calcination, of tungsten or molybdenum; (2) alumina promoted by an oxide, or compound convertible to an oxide by calcination, of molybdenum or tungsten; and (3) one or more of the group aluminum phosphate, zirconium phosphate, calcium phosphate, magnesium phosphate, thorium phosphate or titanium phosphate promoted by one or more of an oxide of molybdenum or tungsten, or by a compound of molybdenum or tungsten convertible to an oxide by calcination.

The solid catalysts can be in any conventional catalytic shape or size, depending upon the type of conversion in which it is to be utilized. For example, in fixed bed catalyst systems, the solid composite can be in the form of spheres, pellets, extrudates, agglomerates, and the like. In slurry catalyst systems, the solid can be in the form of relatively small particles or in the form of a powder.

To be effective in the present catalyst system, the above-described component of the catalysts is activated by calcination at elevated temperatures, generally in flowing air. The activation of the catalysts is accomplished at a temperature of from about 300° to about 800° C. for a period of several minutes to several hours or longer. When the solid component of the catalyst system is tungsten oxide on silica, a convenient and economical treatment is in the temperature range of 400°–700° C. for 0.5 to 20 hours or longer. In some cases the activation using an oxygen-containing gas can be followed by treatment, also at elevated temperatures, with other treating gases such as carbon monoxide, hydrogen, and the like.

The oxide of molybdenum or tungsten is preferably combined with the inorganic refractory solid in a high positive oxidation state, e.g., hexavalent molybdenum or hexavalent tungsten. The proportion of the molybdenum or tungsten oxide combined with the inorganic refractory material can be varied, but generally the inorganic refractory material contains at least 0.1 percent by weight of the oxide of molybdenum or tungsten with amounts from about 0.2 percent to about 30 percent by weight being preferred, although still larger (major) proportions of molybdenum or tungsten oxide can be used. The weight percent referred to is based on the combined weights of the refractory material and the metal.

The promoting or treating agent can be combined with the thus prepared catalyst in any suitable manner. For example, the catalyst is impregnated with a liquid diluent containing the promoting agent. After impregnation the catalyst is then heated in an inert atmosphere, such as nitrogen or argon, to remove the liquid diluent. The temperature employed in removing the diluent and activating can vary widely; however, temperatures in the range of about 400° C. to about 800° C. are currently preferred. If desired, the promoting agent can be applied to the catalyst in a reaction zone by spraying or otherwise contacting the catalyst. It is also contemplated that the promoting agent can be introduced along with olefin feed for contacting with the catalyst.

In accordance with the invention, calcined, tungsten and molybdenum oxide refractory material catalysts are treated with an effective catalytically promoting amount of at least one of a chlorinated silicon compound, thionyl chloride, and sulfuryl chloride, and heated under conditions to form a promoted catalyst. Suitable chlorinated silicon compounds that can be used include monosilanes, siloxanes, and polysilanes.

Monosilanes that can be used have the formula $$SiCl_nR_{4-n}$$

wherein R is hydrogen, a hydrocarbyl group, such as alkyl, cycloalkyl, aryl, alkaryl, and the like, or a halogenated hydrocarbyl group, and n is an integer of 1 to 4.

Representative examples of these compounds include monomethyl-tri-chlorosilane, isobutyltrichlorosilane, dimethyldichlorosilane, trimethyl monochlorosilane, n-decyldichlorosilane, trichloromethyltrichlorosilane, 4-methylphenyltrichlorosilane, monochloromethyltrichlorosilane, cyclohexyldichlorosilane, and the like, and mixtures thereof.

Siloxanes that can be used have the formula $$R_{6-m}Si_2OCl_m$$

wherein m is an integer of 1 to 6 and R is as defined above.

Representative examples of these siloxane compounds include chlorodisiloxane, 1-chloro-d,d-dichlorodisiloxane, hexachlorodisiloxane, 1-methyl-2,2,2-trichlorodisiloxane, 1-isopropyl-1-chloro-2,2-dichlorodisiloxane, 1-trichloromethyl-2,2-dichlorodisiloxane, pentachlorodisiloxane, 1-cyclopentyl-2,2-dichlorodisiloxane, 1,1-dimethyl-2,2,2-trichlorodisiloxane, and the like, and mixtures thereof.

Polysilanes that can be used have the formula $$Si_nR_yCl_x$$

wherein n is an integer of 2 to 6, x is 1 to 2n+2, y is 2n+2−y, and R is as defined above.

Representative examples of these compounds include hexachlorodisilane, 1,1-dimethyl-2,2,2-trichlorosilane, 1,1-dichloro-2-chlorotrisilane, 1,1-dichloro-2,2-dichlorodisilane, 1,1,1-trichloro-2-n-hexyl-4,4,4-trichlorotetrasilane, 1,1,1-trichlorohexasilane, 1-dichloromethyl-2-chlorodisilane, pentachlorodislane, 1,1-dichlorodisilane, 1,1,1-trichloro-2-benzyl-3,3-dichlorotrisilane and the like, and mixtures thereof.

Other treating agents contemplated within the scope of the invention are thionyl chloride ($SOCl_2$) and sulfuryl chloride ($SO_2Cl_2$), including mixtures thereof.

The optimum amounts of catalyst promoting or treating agent employed can readily be determined by routine experimentation. Generally, the promoting agent should be used in an amount in the range of about 0.1 to about 100 weight percent, preferably about 0.1 to about 20 weight percent, more preferably about 5 to about 15 weight percent, based on the total weight of the metal oxide and refractory material prior to the addition of the promoting agent.

The promoted catalyst can be used in disproportionation reactions in a conventional manner. The reaction temperature can vary depending upon the catalyst and feed(s) employed, but will be sufficient to effect disproportionation. Typically, the disproportionation is carried out at a temperature in the range of about 20° to about 600° C.

The disproportionation reaction can be carried out by contacting the olefins to be disproportionated with the catalyst in the liquid phase or the gas phase, depending on structure and molecular weight of the olefins, temperature and pressure.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least one hydrogen atom. Mono-olefins are preferred.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexane, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethylcyclooctadiene-1,4, and the like, and mixtures thereof.

The pressure during the disproportionation reaction may vary between wide limits. Pressures between 0.1 and 500 atm. are suitable; preferred pressures are between 0.5 and 250 atm.

If the reaction is carried out in the liquid phase, solvents or diluents for the reactants may be used. Aliphatic saturated hydrocarbons (e.g., pentane, hexane, cyclohexane, dodecane) and aromatic hydrocarbons such as benzene and toluene are suitable. If the reaction is carried out in the gaseous phase, diluents such as aliphatic hydrocarbons (e.g., methane, ethane) and/or inert gases (e.g., nitrogen, argon) can be present. Preferably the disproportionation reaction is effected in the substantial absence of reactive materials such as water and oxygen.

The length of time during which the olefinically unsaturated compounds to be disproportionated are contacted with the catalyst depends upon several factors such as the activity of the catalyst, temperature, pressure, and structure of the olefinically unsaturated compound to be disproportionated. Contact time can conveniently vary between 5 seconds and 24 hours, although longer and shorter contact times may be used. The contact time needed to obtain a reasonable yield of disproportionated products depends on the factors mentioned above.

The process of the invention is effected batchwise or continuously, with fixed catalyst beds, slurried catalysts, fluidized beds or by using any other conventional contacting technique. The solid disproportionation catalysts are employed in any appropriate form, for example, as powders, flakes, pellets, spheres or extrudates.

The olefinic products of the invention, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

All reactions were carried out in a tubular quartz or 316 stainless steel reactor ($\frac{1}{2}''$ outer diameter) fitted with a thermocouple well centered axially. A thermocouple was positioned in the center of the catalyst bed. The reactor tube was placed in a temperature controlled electric furnace. The catalysts employed were ground to $-20+40$ mesh, with 1.5–1.8 g used per run. Catalysts were activated prior to use by heating in flowing nitrogen (about 150 ml/min) at 400°–600° C. for $\frac{1}{2}$–1 hour before cooling to the desired reaction temperature.

Regeneration, when carried out, was performed by treating catalyst at about 600° C. in flowing air (about 200 ml/min) for about one hour, followed by nitrogen purge (about 200 ml/min) and the same temperature. Phillips polymerization grade propylene was used as feedstock. Feed propylene was pretreated with Alcoa H151 activated alumina and activated magnesia. Reaction product was analyzed by gas liquid chromatography (GLC) employing a Hewlett-Packard model 5880A chromatograph with a $\frac{1}{8}''\times 20'$ column packed with 19 percent BMEE+1 percent squallene on 60/80 Chrom P. Analyses were carried out isothermal at a temperature of 30°–40° C. with a helium carrier gas flow rate of about 20 ml/min. In all runs reported, selectivity to disproportionation products, i.e., $C_2+C_4$ olefins, was essentially quantitative.

The $WO_3.SiO_2$ catalyst used in the following runs was prepared by impregnating silica gel with an aqueous solution containing 0.0727 g of ammonium metatungstate ($(NH_4)_2W_4O_{13}.8H_2O$) per g of silica. The catalyst was dried by any suitable means, then calcined in air at at least 500° C. for 30 minutes or longer to convert the metatungstate to the oxide. The resulting catalyst contained about 6 weight percent $WO_3$ based on the $SiO_2$ support.

EXAMPLE I

Control Runs—$WO_3.SiO_2$

The tubular stainless steel reactor was charged with 1.5 g of $WO_3.SiO_2$ which was prepared as described above. Catalyst was calcined for about 1 hour at 600° C. under an air flow of about 150–200 ml/min, then purged with nitrogen under the same temperature and flow rates for about 20 minutes. Catalyst was then cooled to about 500° C., and propylene introduced at the rate of 150 ml/min. Reaction was carried out for 2 hours or so, with periodic sampling for analysis, then propylene flow discontinued. Results of propylene reaction over fresh catalyst are presented in Table I.

After propylene flow had been discontinued, air flow, at about 150–200 ml/min was begun, and the catalyst bed heated to 600° C. for about 1 hour. Nitrogen purge followed for about 20 minutes under the same conditions, the catalyst cooled to 450° C. and propylene flow begun anew at 150 ml/min. As before, periodic samples were taken for analysis. Results of propylene reaction over regenerated catalyst are also presented in Table I.

TABLE I

| Catalyst (T₁°C.) | Propylene Conversion, mol % (Time on-stream, minutes) | | | | |
|---|---|---|---|---|---|
| | (15) | (30) | (50) | (90) | (120) |
| Fresh (500) | 16.3 | 21.1 | 30.5 | 34.9 | 37.2 |
| Regenerated (450) | 4.8 | 7.2 | 11.5 | 14.4 | 16.0 |

A fresh charge of $WO_3.SiO_2$ catalyst (1.6 g) was placed in the quartz reactor and treated in air (150 ml/min) at 600° C. for 1 hour, then in nitrogen (150 ml/min) at 600° C. for 1 hour. Reactor was then cooled to 400° C., and propylene introduction commenced at a rate of 150 ml/min. Samples were taken periodically for analysis, see results presented in Table II (entry 1). Once propylene flow was stopped, air flow was reintroduced (150 ml/min) for 1 hour with catalyst warmed to 600° C., then the catalyst was purged with nitrogen (150 ml/min) for 30 minutes. The reactor was again cooled to 400° C., and propylene flow of 150 ml/min begun. As before, periodic samples were taken, with results summarized in Table II (entry 2).

A fresh charge of $WO_3.SiO_2$ (1.5 g) was activated by heating to 600° C. for 1 hour under an air flow of 200 ml/min, followed by nitrogen flow of 200 ml/min at 600° C. for 30 minutes. Catalyst was then cooled to 400° C. for introduction of propylene at about 160 ml/min. As before, periodic samples were taken, with results summarized in Table II (entry 3).

TABLE II

| Catalyst (T₁°C.) | Entry | Propylene Conversion, mol % (Time on-stream, minutes) | | | | |
|---|---|---|---|---|---|---|
| | | (26) | (47) | (68) | (89) | (150) |
| Fresh (400) | 1 | 18.4 | 17.3 | 16.0 | 14.9 | 13.3 |
| Regenerated (400) | 2 | 15.2 | 14.6 | 14.2 | 13.7 | — |
| Fresh (400) | 3 | 14.3 | 16.3 | 18.1 | 17.8 | — |

The results of these experiments demonstrate the $WO_3.SiO_2$ catalyst is effective for conversion of propylene via disproportionation to $C_2 + C_4$ olefin products.

EXAMPLE II

$WO_3.SiO_2$ Treatment with Silicon Compounds

Several treated $WO_3.SiO_2$ catalysts were prepared for evaluation for the disproportionation of propylene.

(A) A 15 volume percent solution of $Si_2Cl_6$ in hexane was placed in a bubbler. A nitrogen stream (200 ml/min) was passed through the $Si_2Cl_6$ containing solution at room temperature and over 1.5 g of fresh $WO_3.SiO_2$ catalyst prepared as described above. The catalyst bed in a quartz reactor was heated to 400° C. After $Si_2Cl_6$ saturated nitrogen had been passed over heated catalyst for about 30 minutes, dry nitrogen was passed over the catalyst for about 20 minutes (200 ml/min, 400° C.). Propylene was then introduced. See Table III for results.

(B) Fresh $WO_3.SiO_2$ catalyst (1.5 g) was placed in the tubular stainless steel reactor. A 1.0 ml aliquot of $Si_2Cl_6$ was injected into the top of the reactor with a syringe, catalyst bed then heated to 550° C. under air flow (about 150 ml/min) for about 1 hour, then nitrogen was introduced at 150-200 ml/min and 600° C. for about one hour. The catalyst was then cooled to 450° C. and propylene flow started. See Table III for results.

(C) A 1.6 g aliquot of fresh $WO_3.SiO_2$ was treated with 2.5 ml of $SiCl_3CCl_3$ (25% solution in toluene), washed with pentane and dried. 1.5 g of treated catalyst was placed in the tubular quartz reactor, treated at 400° C. under a nitrogen atmosphere (200 ml/min) for 1 hour, then propylene introduction started. See Table III for results.

(D) Fresh $WO_3.SiO_2$ catalyst (1.5 g) was placed in the tubular quartz reactor. A 1.5 ml aliquot of $BrSiCl_3$ was injected into the top of the reactor with a syringe, the catalyst bed was then swept with $N_2$ at 200 ml/min and 400° C. for about 90 minutes before propylene feed was introduced. See Table III for results.

(E) Fresh $WO_3.SiO_2$ catalyst (1.5 g) was placed in the tubular quartz reactor. A 1.5 ml aliquot of $ClH_2C-SiCl_3$ was injected into the top of the reactor with a syringe. Catalyst bed was then heated to 400° C. for about 90 minutes under a nitrogen flow of 200 ml/min, then propylene flow started. See results in Table III.

TABLE III

| Catalyst (T, °C.) | Treating Agent | Propylene, flow rate, ml/min | (Time On-Stream) Propylene Conversion, mol % | | | | | |
|---|---|---|---|---|---|---|---|---|
| A(400) | $Si_2Cl_6$ | 120 | (5) | (26) | (48) | (70) | (91) | (135) |
| | | | 11.1 | 20.3 | 24.0 | 24.3 | 23.6 | 22.8 |
| B(450) | $Si_2Cl_6$ | 150 | (3) | (30) | (45) | (60) | (90) | (120) |
| | | | 39.3 | 44.7 | 44.6 | 44.7 | 44.5 | 44.6 |
| C(400) | $SiCl_3CCl_3$ | 170 | (5) | (25) | (45) | (66) | (87) | (128) |
| | | | 35.7 | 38.2 | 38.7 | 39.0 | 39.1 | 38.9 |
| D(400) | $BrSiCl_3$ | 178 | (5) | (29) | (53) | (76) | (98) | |
| | | | 8.3 | 9.2 | 8.6 | 7.7 | 7.3 | |
| E(400) | $ClH_2CSiCl_3$ | 160 | (5) | (29) | (53) | (77) | (100) | |
| | | | 39.2 | 39.4 | 38.6 | 37.8 | 37.0 | |

The results of these experiments demonstrate that treating a disproportionation catalyst such as $WO_3.SiO_2$ with a variety of chlorosilane compounds gives a large increase in propylene conversion compared to untreated $WO_3.SiO_2$ catalyst. On the other hand, the bromine-containing treating agent (Catalyst D) showed no advantage.

EXAMPLE III

$WO_3.Th_3(PO_4)_4$ Catalyst (F) A 6 percent $WO_3$ on thorium phosphate catalyst was prepared by pouring a solution comprising 0.8 g of 85 percent ammonium metatungstate in 13 ml of deionized water over 11.5 g of $Th_3(PO_4)_4$. After standing for a few minutes, the mixture was dried on the hot plate with stirring. 1.6 g of this material was placed in the quartz reactor, treated with air (150 ml/min) for 1 hour at 560° C., then treated with $N_2$ at 100 ml/min as temperature was reduced to 500° C. Propylene was then introduced at the rate of 100 ml/min. See results summarized in Table IV.

(G) A fresh 1.5 g sample of WO$_3$Th$_3$(PO$_4$)$_4$ was placed in the reactor, and 1.5 ml of Cl$_3$C—SiCl$_3$ was injected into the top of the reactor with a syringe. The catalyst bed was swept with N$_2$ at 100 ml/min to aid movement of the chlorosilane through the bed, then heated to 500° C. for 30 minutes under 200 ml/min N$_2$ flow, then propylene feed (100 ml/min) commenced. Results are summarized in Table IV.

TABLE IV

| Catalyst | Time On-Stream Propylene Conversion, mol % | | | | | |
|---|---|---|---|---|---|---|
|  | (5) | (27) | (48) | (68) | (89) | (102) |
| (F) Untreated | 0.8 | 0.6 | 0.5 | 0.4 | — | — |
| (G) Cl$_3$CSiCl$_3$ treated | 1.4 | 3.6 | 4.9 | 5.8 | 6.4 | 6.7 |

The results of these experiments demonstrate that chlorosilane treatment of a disproportionation catalyst such as WO$_3$.Th$_3$(PO$_4$)$_4$ gives a large increase in propylene conversion compared to untreated WO$_3$.Th$_3$.(PO$_4$)$_4$ catalyst.

EXAMPLE IV

SOCl$_2$ Treatment (H) Fresh WO$_3$.SiO$_2$ catalyst (1.6 g) was placed in the quartz reactor tube. A 2 ml aliquot of SOCl$_2$ was allowed to percolate through the catalyst bed, the reactor then heated to 600° C. and flushed with N$_2$ for 1 hour at 150 ml/min. Reactor temperature was then lowered to 400° C. and propylene introduced at a rate of about 160 ml/min. Reaction results are presented in Table V (entry 1).

(I) An alternate treatment with SOCl$_2$ was carried out by adding 0.5 ml of SOCl$_2$ to 1.5 ml of fresh catalyst. The catalyst bed was flushed with N$_2$ at 200 ml/min while the temperature was slowly raised to 400° C., held at that temperature for 30 minutes, then slowly raised further to 600° C. Temperature was maintained at 600° C. for about one hour, then the reactor was cooled to 400° C. and propylene introduced at about 165 ml/min. Reaction results are presented in Table V (entry 2).

(J) The catalyst employed above (entry 2) was regenerated after about 2 hours on-stream. Catalyst was treated under air (200 ml/min) at 600° C. for 1 hour, then under N$_2$ at 200 ml/min for 30 minutes at 600° C., then cooled to 400° C. Propylene was introduced when the reactor reached 400° C. at a rate of about 150 ml/min. Results are presented in Table V (entry 3).

TABLE V

| Catalyst (T, °C.) | Entry | Propylene flow rate, ml/min | Time On-Stream Propylene Conversion, mol % | | | | | | |
|---|---|---|---|---|---|---|---|---|---|
| H(400) | 1 | 160 | (5) | (20) | (47) | (69) | (90) | | |
|  |  |  | 38.9 | 25.4 | 18.1 | 15.6 | 14.2 | | |
| I(400) | 2 | 165 | (5) | (27) | (48) | (69) | (90) | (111) | (132) |
|  |  |  | 43.7 | 44.2 | 45.9 | 43.7 | 43.8 | 43.5 | 43.6 |
| J(400) | 3 | 150 | (5) | (26) | (47) | (68) | (89) | (110) | |
|  |  |  | 42.9 | 43.3 | 43.2 | 42.8 | 40.0 | 35.7 | |

The results of these experiments demonstrate that thionyl chloride treatment of a disproportionation catalyst such as WO$_3$.SiO$_2$ gives a large increase in propylene conversion compared to untreated WO$_3$.SiO$_2$ catalyst. In addition, the beneficial effect is seen to persist after normal catalyst regeneration.

What is claimed is:

1. A process for preparing a disproportionation catalyst comprising forming a catalytically effective amount of calcined composite comprising at least one metal oxide selected from molybdenum oxide and tungsten oxide and an inorganic refractory material, contacting the calcined composite with a promoting amount of at least one treating agent selected from chlorinated silicon compounds comprising monosilanes selected from the group consisting of monomethyl-Tri-chlorosilane, isobutyltrichorosilane, dimethyldichlorosilane, trimethyl monochlorosilane, n-decyldichlorosilane, trichloromethyltrichlorosilane, 4-methylphenyltrichlorsilane, monochloromethyltrichlorosilane, cyclohexyldichlorosilane, siloxanes, and polysilanes, thionyl chloride, and sulfuryl chloride, and subjecting same to conditions suitable for said treating agent to promote the activity of said molybdenum and tungsten oxides for the disproportionation of olefins.

2. A process according to claim 1 wherein said treating agent is admixed in solution and the resulting composition is dried at a temperature in the range of about 400° C. to about 800° C. in an inert atmosphere.

3. A process according to claim 1 wherein said inorganic refractory oxide is selected from silica and thorium phosphate and further wherein said catalytic amount of said metal oxide is in the range of about 1 to about 10 percent of the combined weights of said metal oxide and said refractory material prior to the addition of the treating agent.

4. A process according to claim 1 wherein the treating agent is employed in an amount in the range of about 0.1 to about 100 weight percent based on the weight of the metal oxide-refractory material combination prior to the addition of the treating agent.

5. A process according to claim 1 wherein said composite is calcined by activating with an oxygen-containing gas at a temperature of from about 300° C. to about 800° C. prior to contacting with treating agent.

6. A process according to claim 5 wherein said calcined composite is impregnated with a solution of treating agent and the resulting composition is dried by heating at a temperature of 400° C. to about 800° C. in an inert atmosphere.

7. A process according to claim 6 wherein the refractory oxide is silica or thorium phosphate and the treating agent is hexachlorodisilane, trichloromethyltrichlorosilane, mono-chloromethyltrichlorosilane, or thionyl chloride.

8. A process according to claim 5 wherein said mono silane is trichloromethyltrichlorosilane or monochloromethyltrichlorosilane.

9. A process according to claim 5 wherein said treating agent is a polysilane having the formula

wherein n is an integer of 2 to 6, x is 1 to 2n+2, y is 2n+2−y, and R is hydrogen, a halogen other than chlorine, a hydrocarbyl group having 1 to 20, inclusive, carbon atoms, or a halogenated hydrocarbyl.

10. A process according to claim 9 wherein said polysilane is hexachlorodisilane.

* * * * *